United States Patent [19]
Root et al.

[11] Patent Number: 5,870,790
[45] Date of Patent: Feb. 16, 1999

[54] POWERED WATER SUBMERSIBLE SCRUBBING DEVICE

[76] Inventors: Jeffrey T. Root, 6231 Thom Rd., Graham, N.C. 27253; Lawrence Kluge, 1955 Raywood Dr., Suite 103, Northbrook, Ill. 60062

[21] Appl. No.: 691,741

[22] Filed: Aug. 2, 1996

[51] Int. Cl.⁶ .................................................. A46B 13/02
[52] U.S. Cl. .................................. 15/22.1; 15/23; 15/28
[58] Field of Search .............................. 15/73, 22.1, 23, 15/28, 97.1, 102, 74

[56] References Cited

U.S. PATENT DOCUMENTS

| | | |
|---|---|---|
| 590,871 | 9/1897 | Abrell . |
| 1,218,936 | 3/1917 | Ford . |
| 1,462,598 | 7/1923 | Grenzke . |
| 1,831,684 | 11/1931 | Petersen . |
| 2,579,393 | 12/1951 | Modrey . |
| 2,944,271 | 7/1960 | Foster . |
| 3,029,451 | 4/1962 | Barr ........................................... 15/23 |
| 3,343,192 | 9/1967 | Goldstein . |
| 3,380,093 | 4/1968 | Hill . |
| 3,407,431 | 10/1968 | Melnik . |
| 3,431,571 | 3/1969 | Kraus . |
| 3,935,909 | 2/1976 | Mabuchi . |
| 3,947,909 | 4/1976 | Kuo . |
| 4,137,588 | 2/1979 | Sandt ........................................ 15/23 |
| 4,228,559 | 10/1980 | Kirk . |
| 4,299,004 | 11/1981 | Lancaster ................................. 15/97.1 |
| 4,574,414 | 3/1986 | Zhadanov . |
| 5,307,537 | 5/1994 | Essex . |
| 5,353,461 | 10/1994 | Enriquez . |
| 5,406,669 | 4/1995 | Lesiw . |

FOREIGN PATENT DOCUMENTS

| | | | |
|---|---|---|---|
| 0692970 | 8/1964 | Canada ................................ 15/22.1 |
| 1023565 | 12/1952 | France ................................. 15/23 |
| 2407106 | 2/1976 | Germany ............................ 15/22.1 |
| 2838015 | 3/1979 | Germany ............................ 15/22.1 |

*Primary Examiner*—Randall E. Chin
*Attorney, Agent, or Firm*—B. Craig Killough

[57] ABSTRACT

A submersible scrubbing device using a direct current electric motor powered by rechargeable batteries. The device has a longitudinal body, with the rotating brush tool positioned in line with the body, to allow the tool and the device to be inserted into narrow passageways. The housing of the device is designed to prevent water from entering the device. Variously configured scrubbing brushes or scrubbing tools are used with the device.

22 Claims, 21 Drawing Sheets

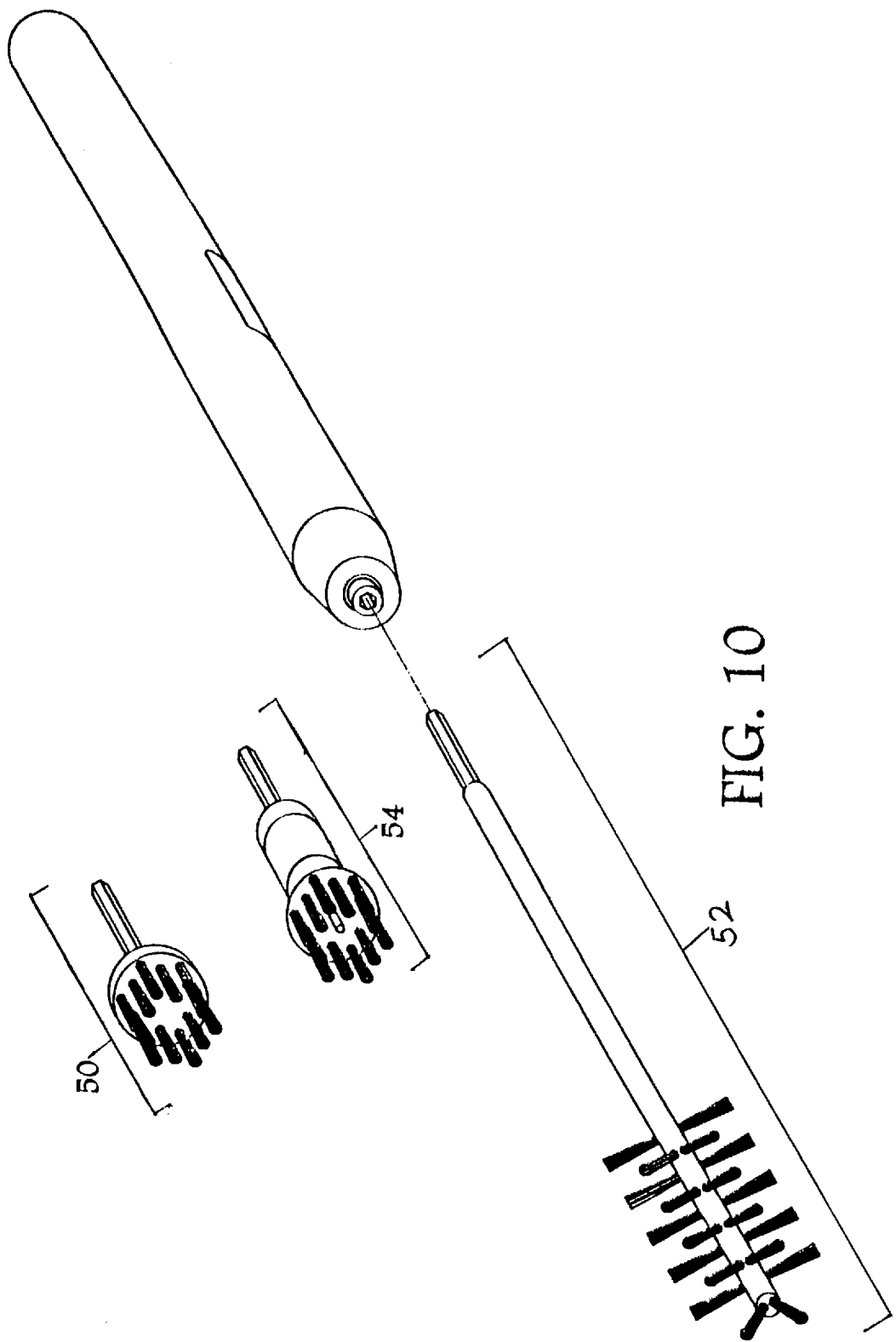

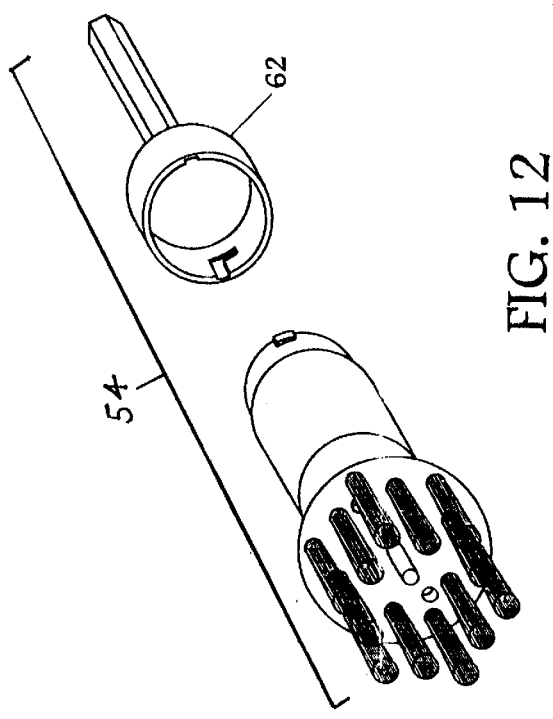
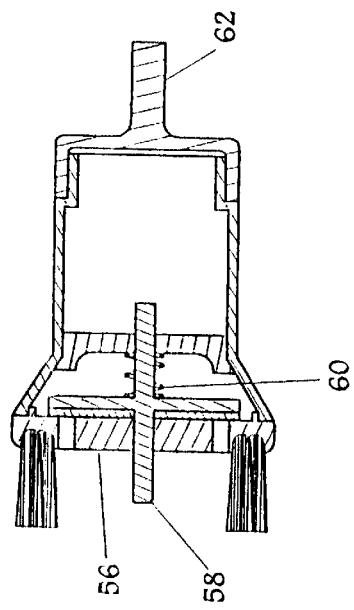
FIG. 12
FIG. 11

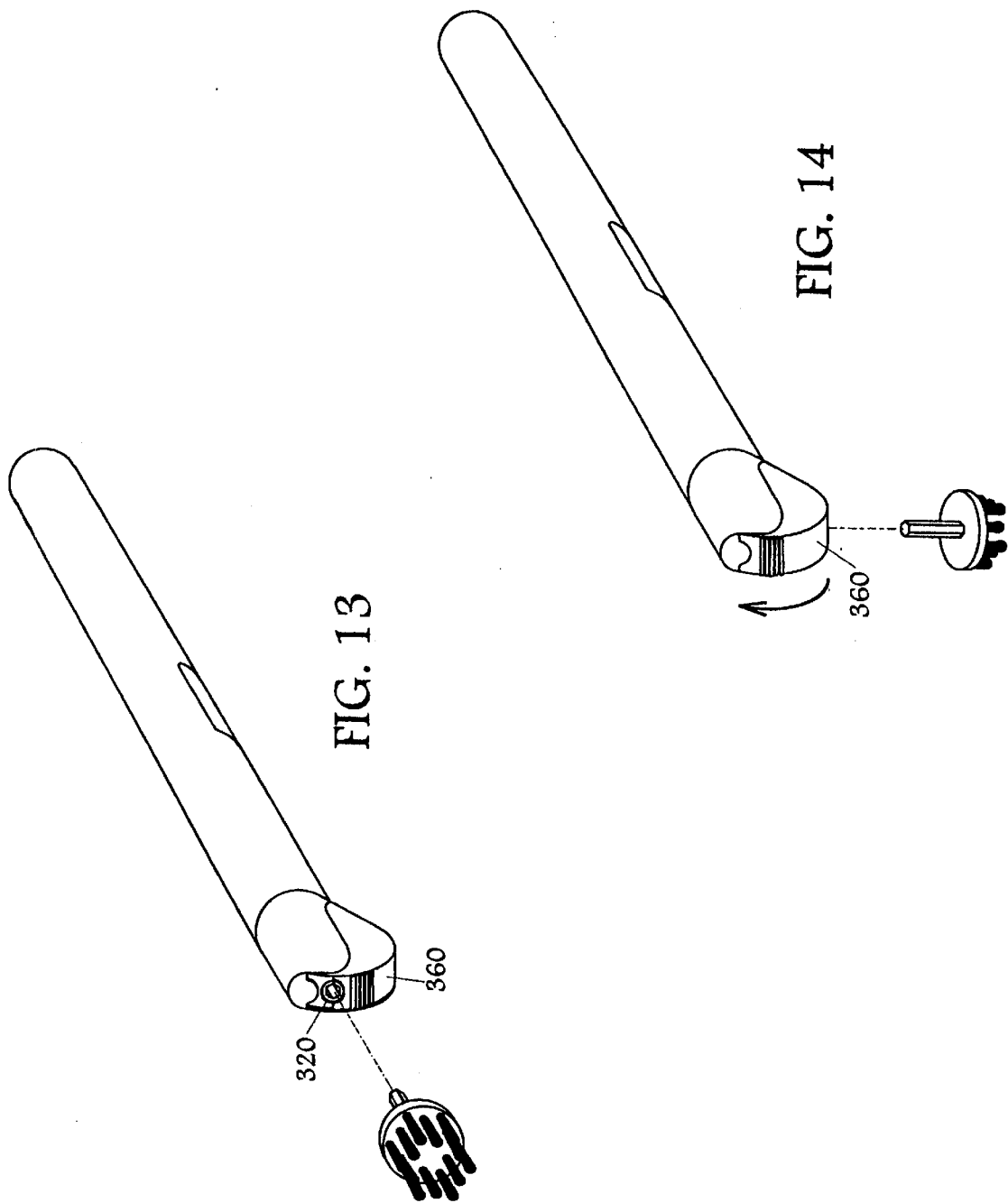

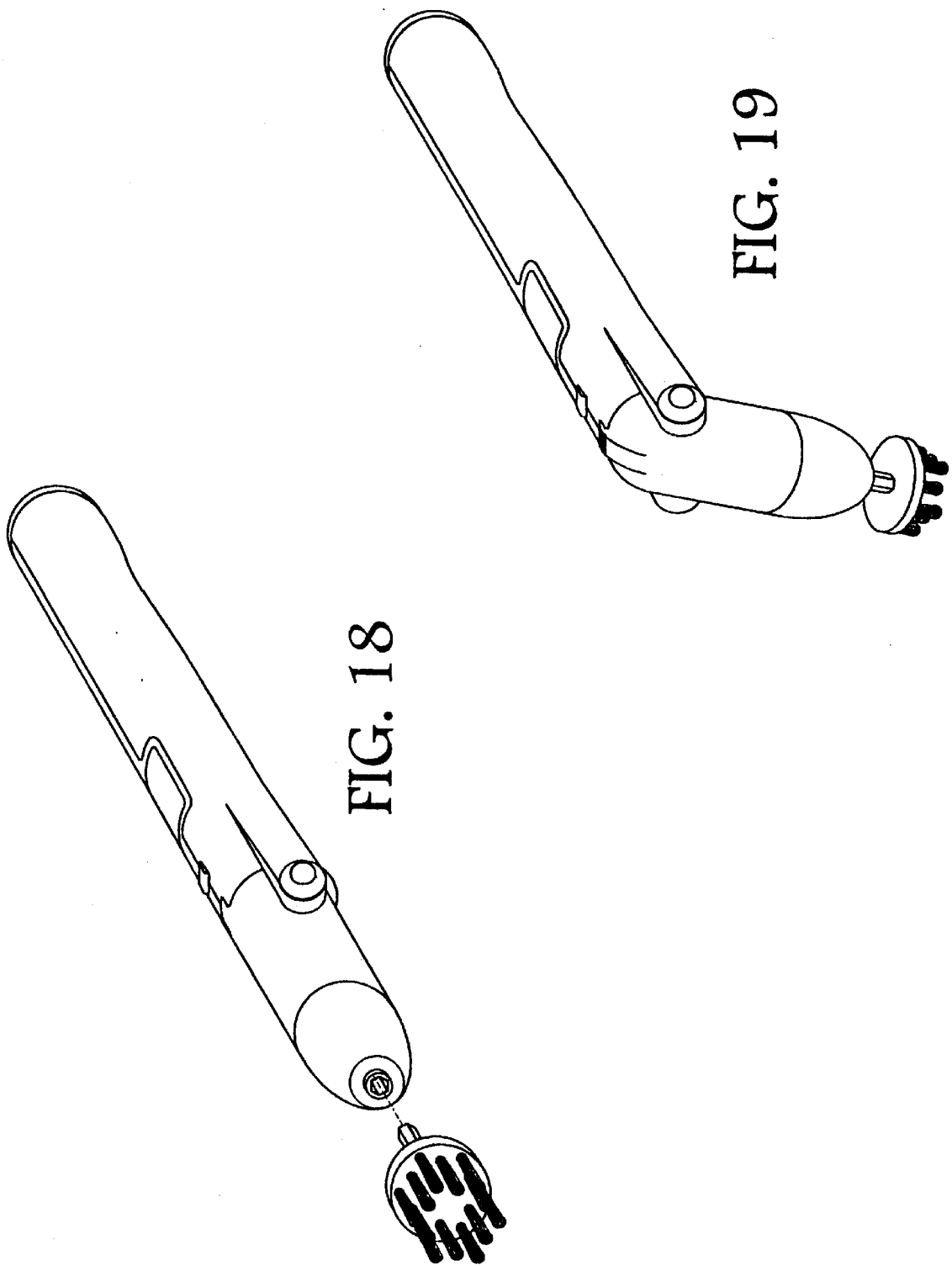

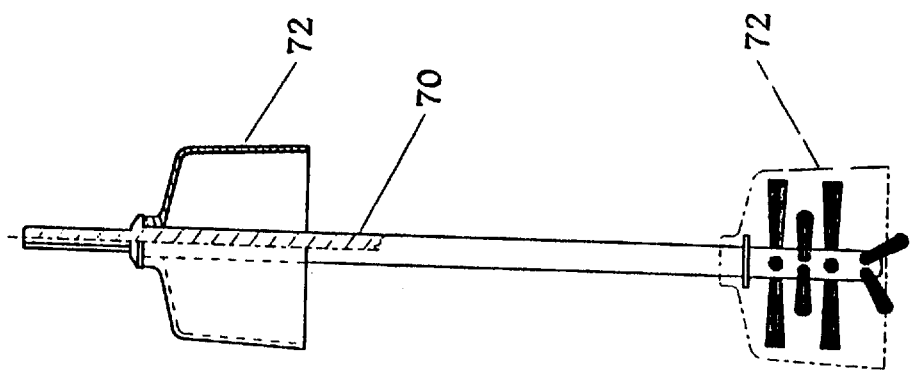

POWERED WATER SUBMERSIBLE SCRUBBING DEVICE

FIELD OF THE INVENTION

This invention relates to hand held powered devices generally, and is more specifically related to a hand held scrubbing device which is water submersible, and preferably, battery-powered.

BACKGROUND OF THE INVENTION

Hand held, battery powered devices having rotary action are known in the art. Examples of these devices are battery powered screwdrivers and drills. The hand held, battery powered, tools of the prior art are characterized by a motor which drives the tool. A rechargeable battery is commonly used to provide direct current to the motor. These devices allow tools to be removably attached, such as by means of insertion of the tool into a tool holder or chuck. These tools may include variously sized screwdriver blades, or variously sized drills.

The hand held battery powered tools of the prior art which have rotary action typically are not water submersible. Accordingly, these devices cannot be used with tools such as brushes in an environment in which a substantial amount of water is present. An example of such an environment is the process of washing dishes, which presents a hostile environment of water of an elevated temperature along with chemicals to aid in cleaning.

Rotary scrubber devices are found in the prior art. However, devices such as Enriquez, U.S. Pat. No. 5,353,461, turn the direction of rotation ninety degrees (90°) from the body of the device. This arrangement prevents the device from being capable of insertion into, for example, glassware which have long, narrow internal cavities for the purpose of cleaning the inside of the glassware.

SUMMARY OF THE PRESENT INVENTION

The present invention is a submersible scrubbing device. Variously configured scrubbing brushes or scrubbing tools may be used with the device. The device is preferably powered by a direct current electric motor, which is powered by rechargeable batteries.

The device of the present invention has a longitudinal body, with the rotating brush tool positioned in line with the body, to allow the tool and the device to be inserted into narrow passageways. The battery and the motor are positioned relatively close to the tool, so that the device is properly balanced in the hand. The shell or encasement of the device allows the device to be water submersible. Accordingly, it is not necessary to position the motor and batteries far away from the tool, and a desired weight distribution of the device while held in the hand is achieved.

DESCRIPTION OF THE DRAWINGS

FIG. 10 is a perspective view of various brush tools which may be used with the device.

FIG. 11 is a sectioned view of a soap brush which may be used with the device.

FIG. 12 is a perspective view of a soap dispensing brush.

FIG. 13 is a perspective view of another embodiment of the device.

FIG. 14 is a perspective view of the device shown in FIG. 13.

FIG. 18 is a perspective view of another embodiment of the device.

FIG. 19 is a perspective view of the device shown in FIG. 18.

FIG. 24 is a sectioned view of an embodiment of a bottle brush for use with the device.

DETAILED DESCRIPTION OF THE PREFERRED EMBODIMENTS

Figure 2:
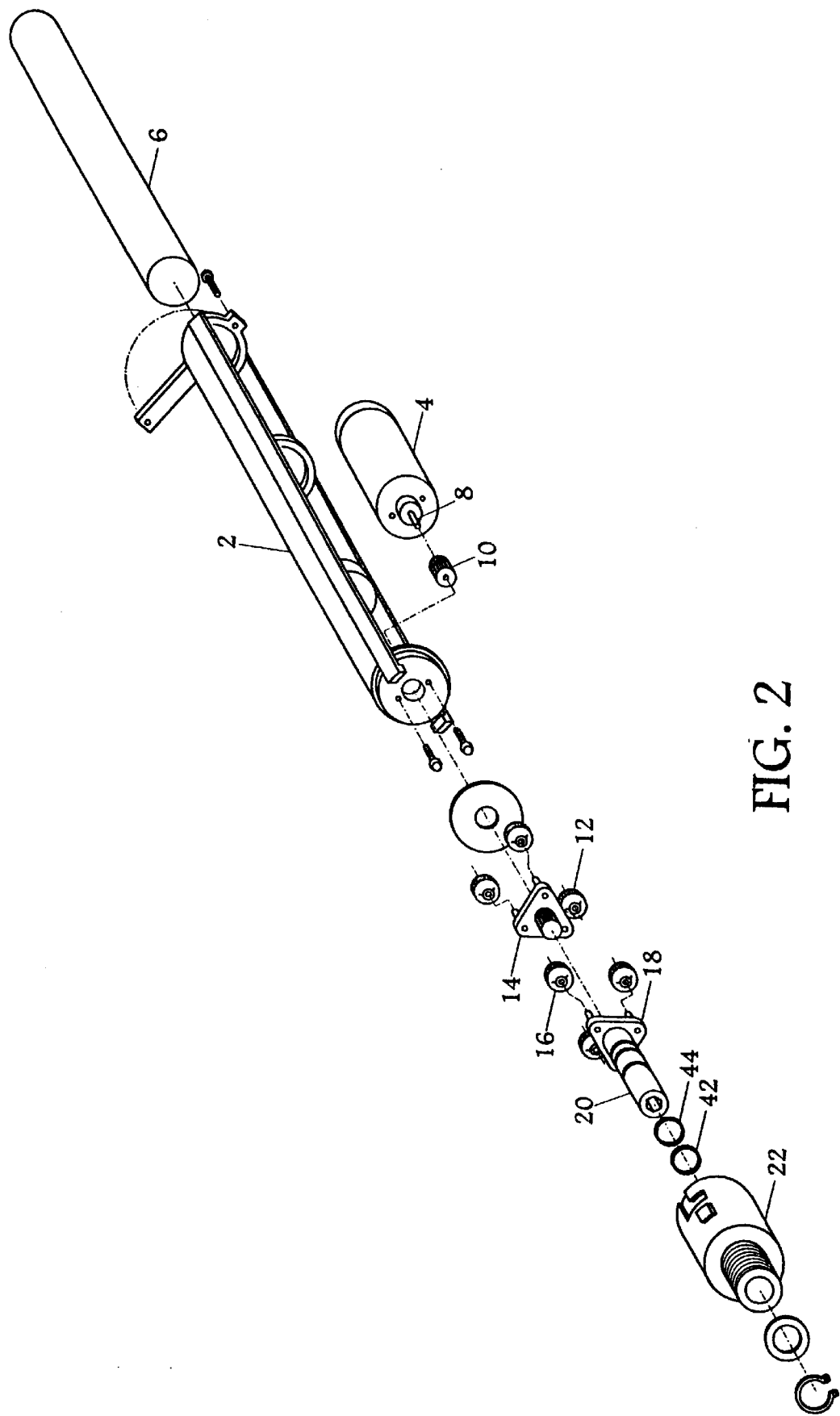
FIG. 2 is an exploded view of an embodiment of the device.

Referring now to the drawing figures, FIG. 2 shows an exploded view of the power train cartridge. A cradle 2 is provided, in which a motor 4 and a rechargeable battery 6 are positioned. The cradle is elongated with the motor positioned near one end thereof, and battery is positioned in contact with the motor in the opposite end of the cradle. The motor shaft 8 extends through an end plate of the cradle, and a pinion 10 is present on the motor shaft. The pinion engages a set of first stage planetary gears 12. The first stage of planetary gears are positioned on the first stage planetary gear carrier 14. A set of second stage planetary gears 16 is provided, which are positioned on the second stage planetary gear carrier 18. The second stage planetary gear carrier, is, in turn, connected to the output shaft 20. The planetary gear train, which is comprised of the first stage planetary gear and the second stage planetary gears, reduces the rotational speed at the output shaft in comparison to the motor, and increases the torque at the output shaft in comparison to the motor.

A planetary gear housing 22 is provided. The planetary gear train is contained within the planetary housing. The planetary housing is connected to the end of the cradle, as shown. The output shaft extends through an end of the planetary housing. The planetary housing, when combined with the cradle, forms a power train cartridge 24.

Figure 3:
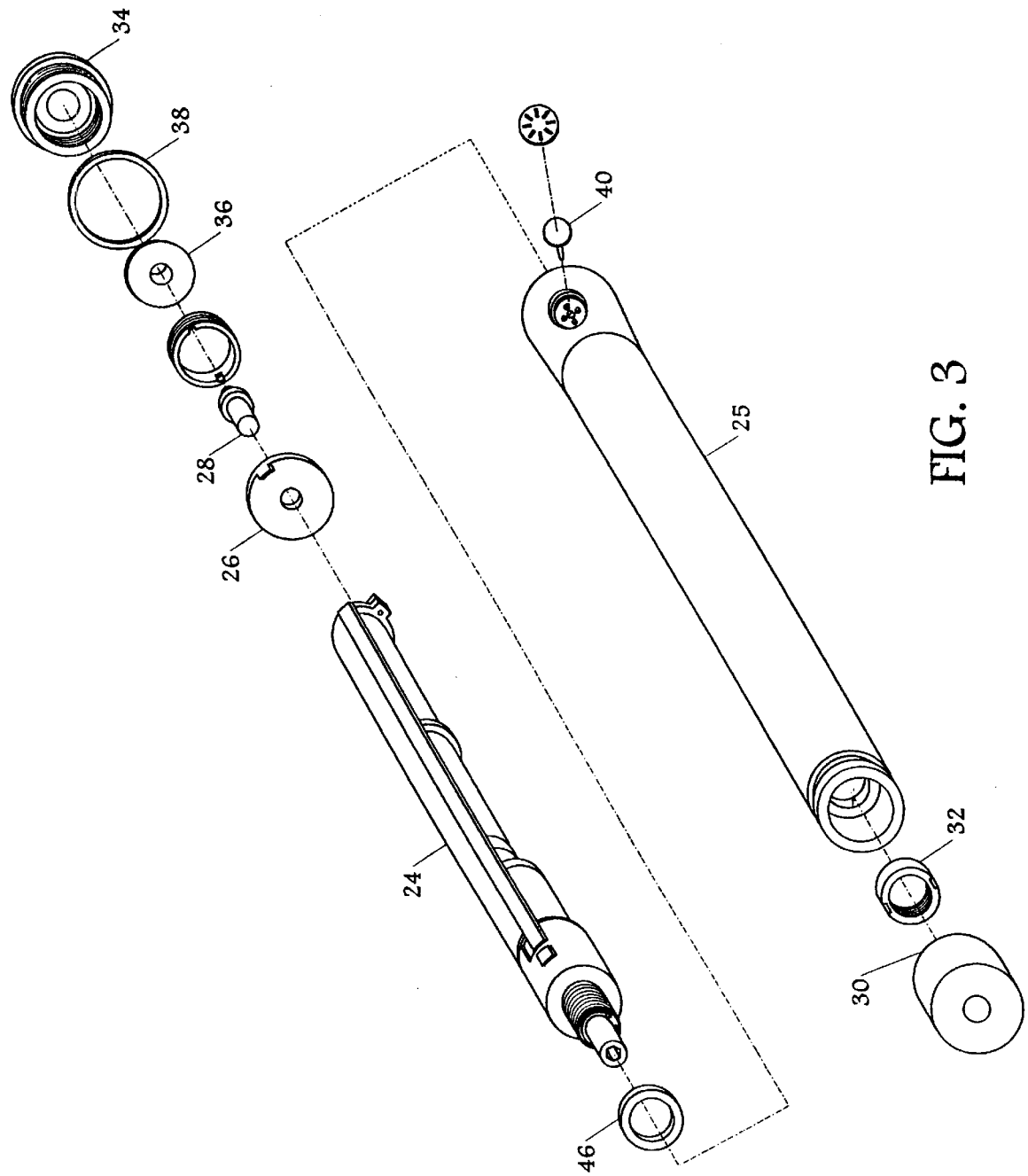
FIG. 3 is an exploded view of an embodiment of the device.

Referring now to FIG. 3, the power train cartridge has a switch plate 26 mounted to the cradle near the end where the battery is positioned. A switch 28 is provided within the switch plate, which may be selectively positioned to allow a current to flow from the battery to the motor, so as to actuate the motor.

The power train cartridge is inserted into the shell 25 as shown in FIG. 3, with the output shaft extending from one end of the shell, and through a primary debris shield 30. The power train cartridge is retained within the shell by means of a lock nut 32 which engages the planetary housing. The primary debris shield may be attached to the shell such as by threading it onto the shell. An end cap 34 may be attached, such as by threading it onto the opposite end of the shell.

The switch 28 extends into a membrane 36, which provides a seal between the switch and the end cap. The switch extends through the end cap. An end cap seal 38 is also provided to prevent water from entering the shell.

A valve may be provided within the shell. The umbrella valve or gas permeable membrane 40 allows gases to exit the shell, in the event gases accumulate within the shell, for example, as a result of recharging the batteries. The valve or gas permeable membrane prevent water from entering the shell.

Figure 1:
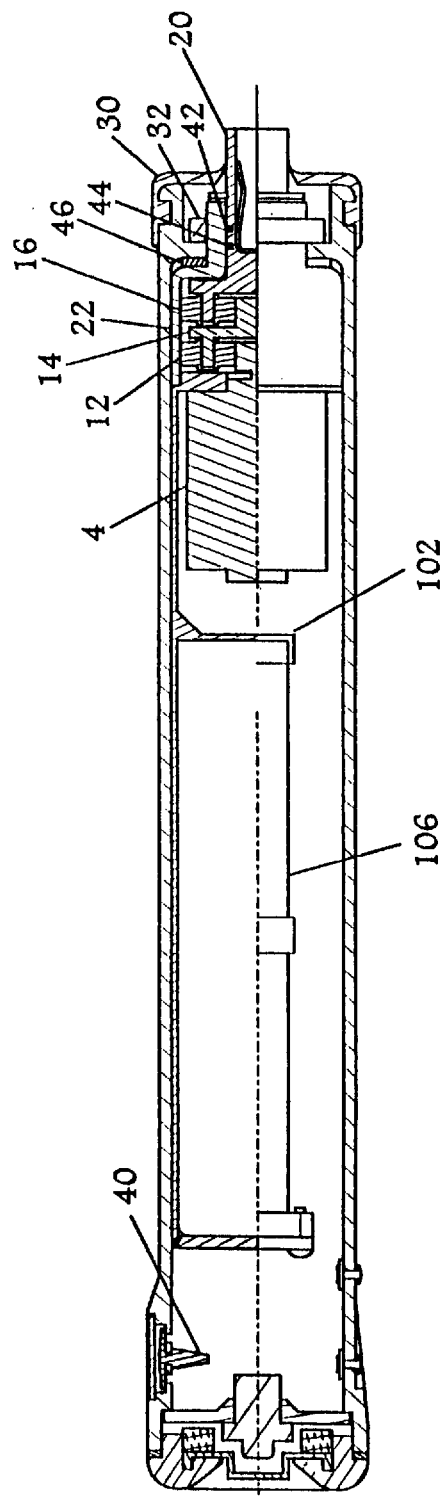
FIG. 1 is a sectioned view of an embodiment of the device.

The sealing arrangement for the device is shown in FIG. 1 and FIG. 2. Multiple seals 42,44 are provided on the output shaft, along the surface of the output shaft which engages the inside diameter of one end of the planetary housing. The shaft seals 42,44 prevent water from entering the power train cartridge between the planetary housing, and the output shaft. A housing seal shown in FIG. 1 and FIG. 3, housing seal 46 is provided between the end of the planetary housing and the shell. As the lock nut 32 engages the threads on the end of the planetary housing, the housing seal is pulled against the shell, to prevent water from entering the shell. The primary debris shield 30 aids in preventing water from entering the shell and the power train cartridge, but is primarily present to prevent solid particulate matter from entering the shell and the power train cartridge. It is anticipated that the device will be used with cleaners, including abrasives which are sold in powdered form, like Ajax . The primary debris shield is sufficient to keep the bulk of such materials out of the shell. The combination of seals and membranes is sufficient to keep water and other foreign substances from entering the shell and the power train cartridge.

Figure 5:
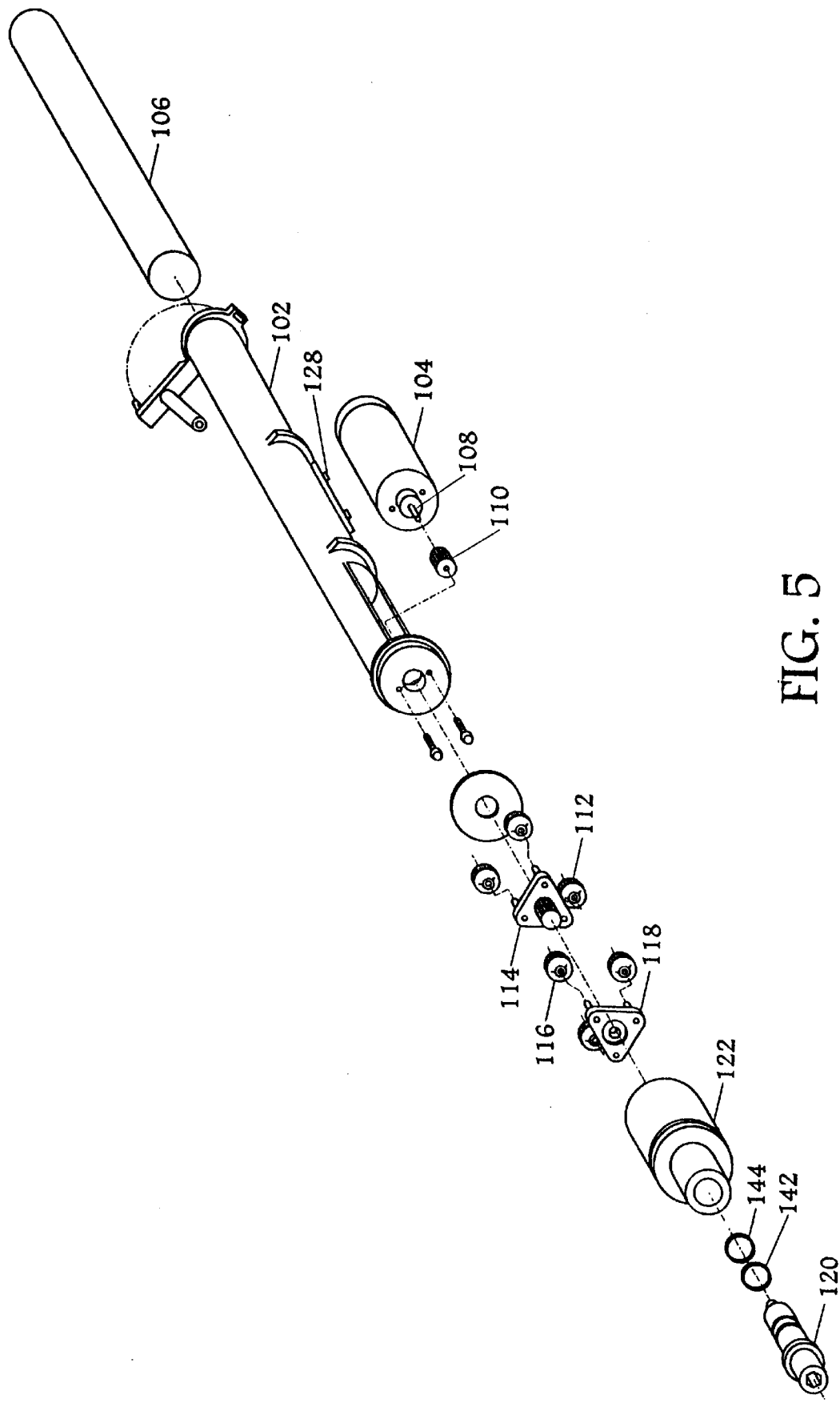
FIG. 5 is an exploded view of the embodiment of the device of FIG. 4.

FIG. 5 shows an exploded view of the power train cartridge of another embodiment of the device. A cradle 102 is provided, in which a motor 104 and a rechargeable battery 106 are positioned. The cradle is elongated with the motor positioned near one end thereof, and battery is positioned in contact with the motor in the opposite end of the cradle. The motor shaft 108 extends through an end plate of the cradle, and a pinion 110 is present on the motor shaft. The pinion engages a set of first stage planetary gears 112. The first stage of planetary gears are positioned on the first stage planetary gear carrier 114. A set of second stage planetary gears 116 is provided, which are positioned on the second stage planetary gear carrier 118. The second stage planetary gear carrier, is, in turn, connected to the output shaft 120. The planetary gear train, which is comprised of the first stage planetary gear and the second stage planetary gears, reduces the rotational speed at the output shaft in comparison to the motor, and increases the torque at the output shaft in comparison to the motor.

A planetary gear housing 122 is provided. The planetary gear train is contained within the planetary housing. The planetary housing is connected to the end of the cradle, as shown. The output shaft extends through an end of the planetary housing. The planetary housing, when combined with the cradle, forms a power train cartridge 124.

Figure 6:
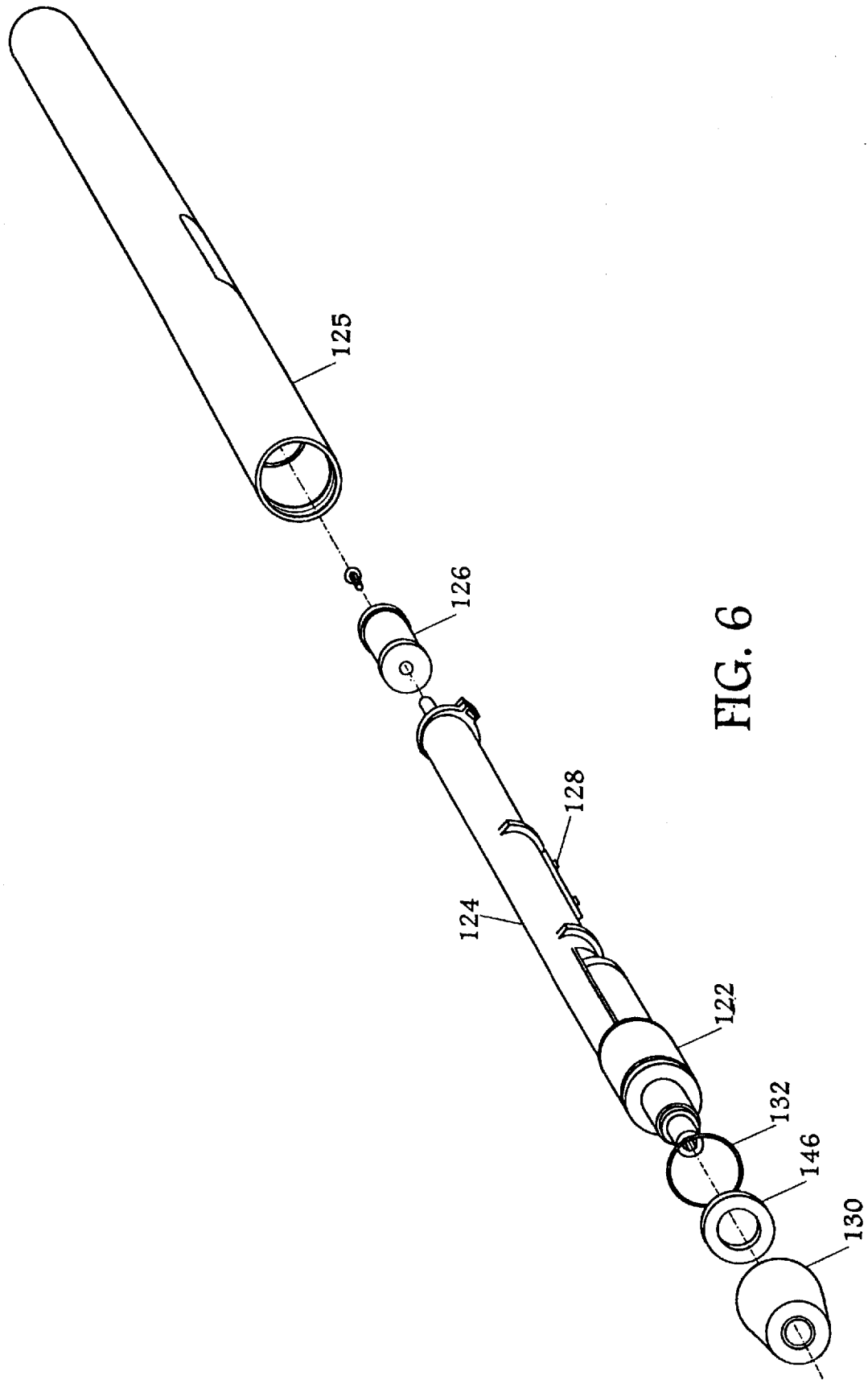
FIG. 6 is an exploded view of the device of the embodiment of FIG. 4.

Referring now to FIG. 6, the power train cartridge has an inductive charging coil 126 mounted to the cradle near the end where the battery is positioned. A switch 128 is provided within the cradle, which may be selectively positioned to allow a current to flow from the battery to the motor, so as to actuate the motor. A switch membrane 136 may be provided as a water seal.

The power train cartridge is inserted into the shell 125 as shown in FIG. 6, with the output shaft extending from one end of the shell, and through an end cap 130. The power train cartridge is retained within the shell by means of the end cap engaging the shell, such as by threading it onto the shell at one end of the shell. The opposite end of the shell is closed.

Figure 4:
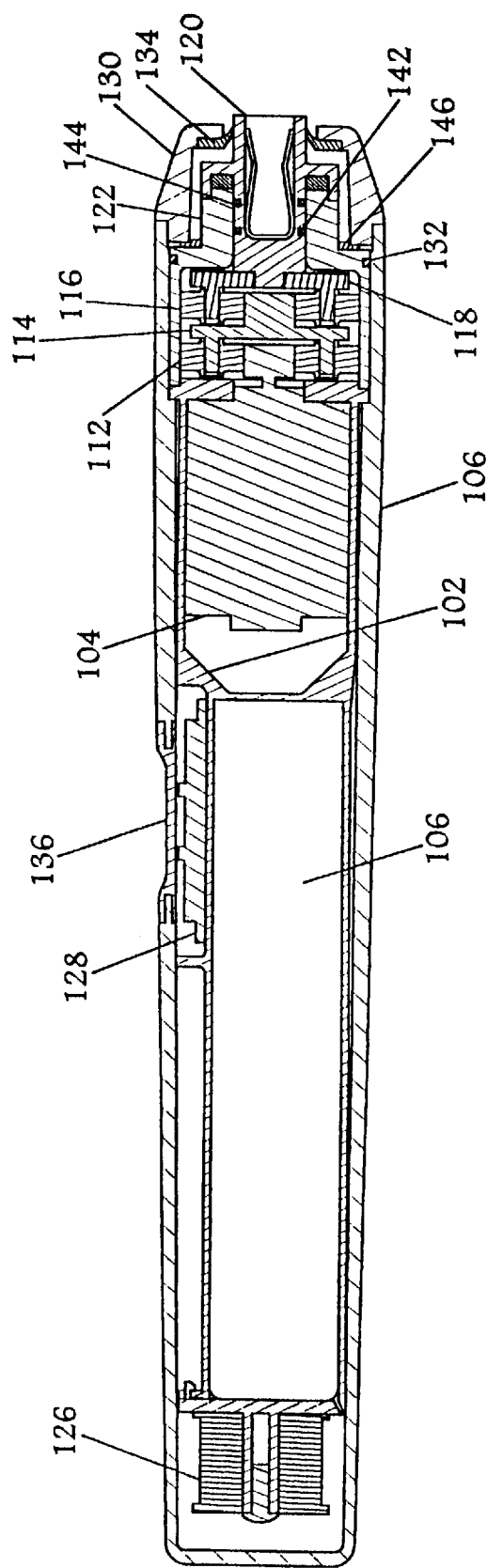
FIG. 4 is a sectioned view of another embodiment of the device.

The sealing arrangement for the device is shown in FIG. 4. Multiple seals 142,144 are provided on the output shaft, along the surface of the output shaft which engages the inside diameter of one end of the planetary housing. The shaft seals 142,144 prevent water from entering the power train cartridge between the planetary housing, and the output shaft. A housing seal 146 is provided between the end of the planetary housing and the shell, and an O ring 132 is provided which seal between the planetary housing and the shell. A debris shield 134 aids in preventing water from entering the shell and the power train cartridge, but is primarily present to prevent solid particulate matter from entering the shell and the power train cartridge. It is anticipated that the device will be used with cleaners, including abrasives which are sold in powdered form, like Ajax . The primary debris shield is sufficient to keep the bulk of such materials out of the shell. The combination of seals and membranes is sufficient to keep water and other foreign substances from entering the shell and the power train cartridge.

Figure 8:
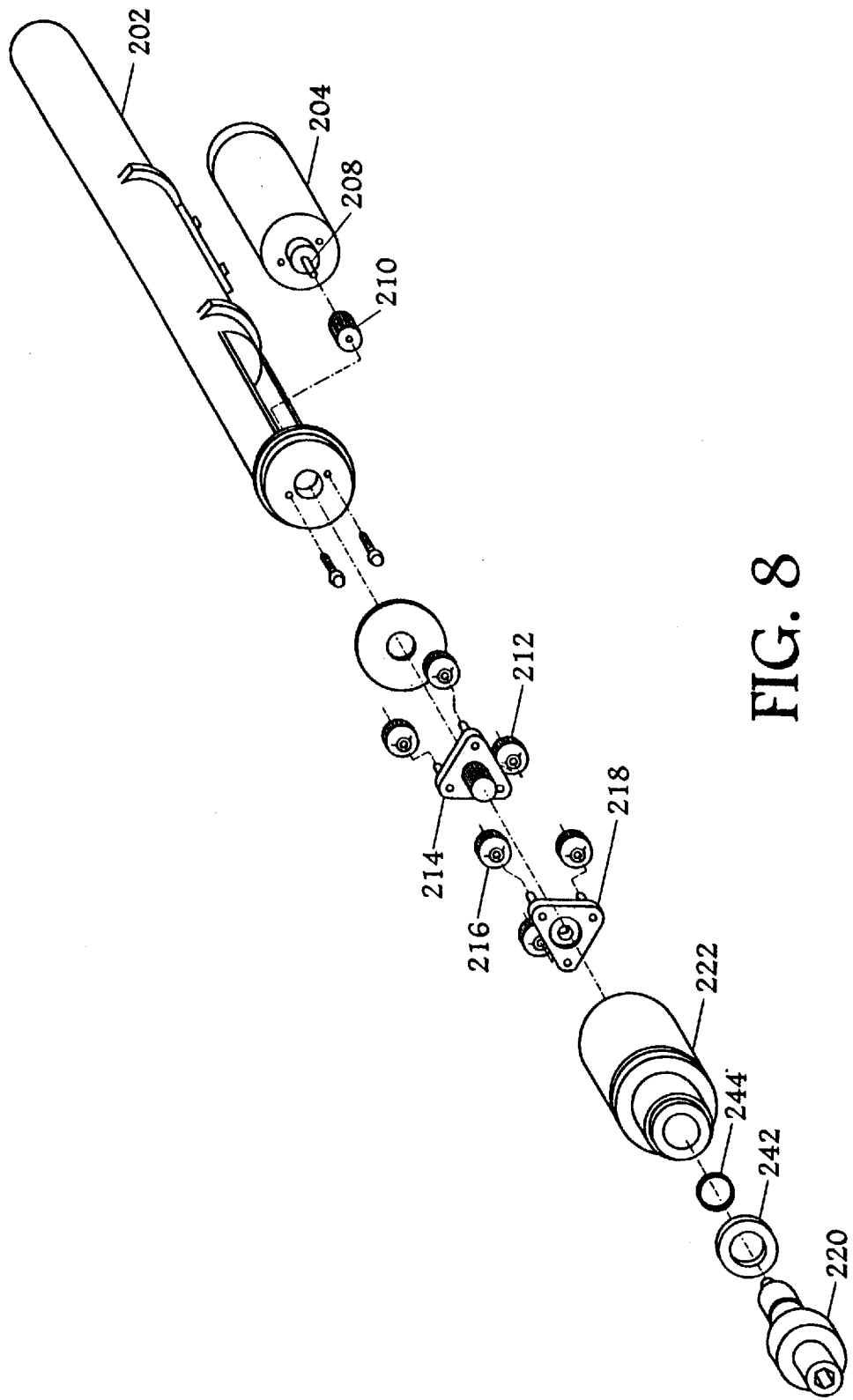
FIG. 8 is an exploded view of the embodiment of the device as shown in FIG. 7.

FIG. 8 shows an exploded view of an additional embodiment of the device. A cradle 202 is provided, in which a motor 204 and a rechargeable battery 206 are positioned. The cradle is elongated with the motor positioned near one end thereof, and battery is positioned in contact with the motor in the opposite end of the cradle. The motor shaft 208 extends through an end plate of the cradle, and a pinion 210 is present on the motor shaft. The pinion engages a set of first stage planetary gears 212. The first stage of planetary gears are positioned on the first stage planetary gear carrier 214. A set of second stage planetary gears 216 is provided, which are positioned on the second stage planetary gear carrier 218. The second stage planetary gear carrier, is, in turn, connected to the output shaft 220. The planetary gear train, which is comprised of the first stage planetary gear and the second stage planetary gears, reduces the rotational speed at the output shaft in comparison to the motor, and increases the torque at the output shaft in comparison to the motor.

Figure 7:
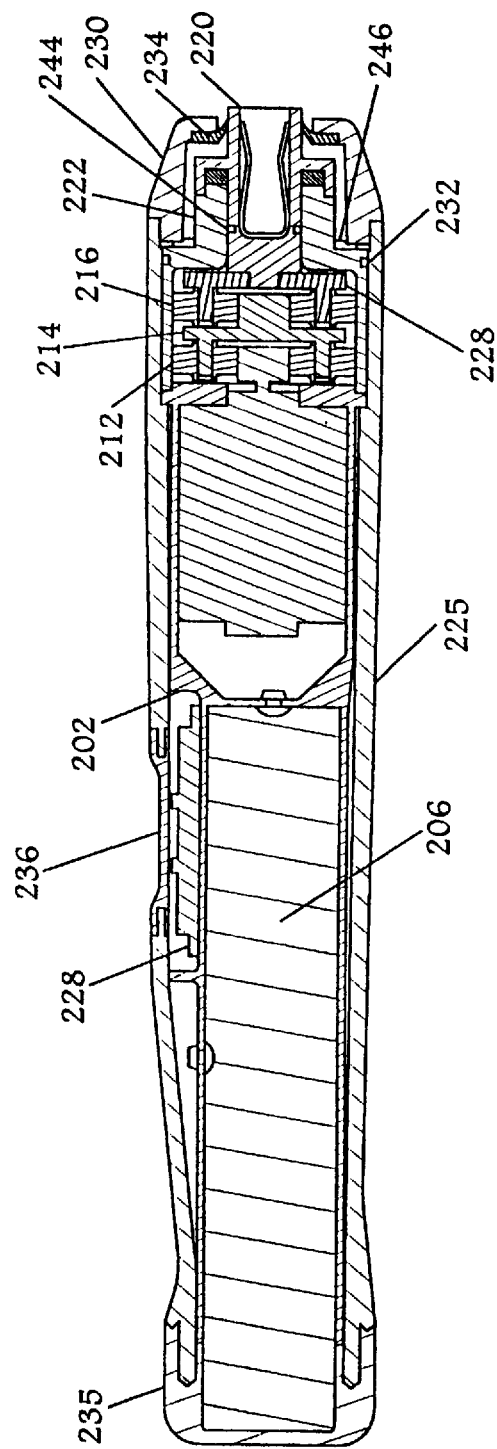
FIG. 7 is a sectioned view of an additional embodiment of the device.

A planetary gear housing 222 is provided. The planetary gear train is contained within the planetary housing. The planetary housing is connected to the end of the cradle, as shown. The output shaft extends through an end of the planetary housing. The planetary housing, when combined with the cradle, forms a power train cartridge 224. Referring now to FIG. 7, the power train cartridge has a switch 228, which may be selectively positioned to allow a current to flow from the battery to the motor, so as to actuate the motor. A switch membrane 236 may be provided.

Figure 9:
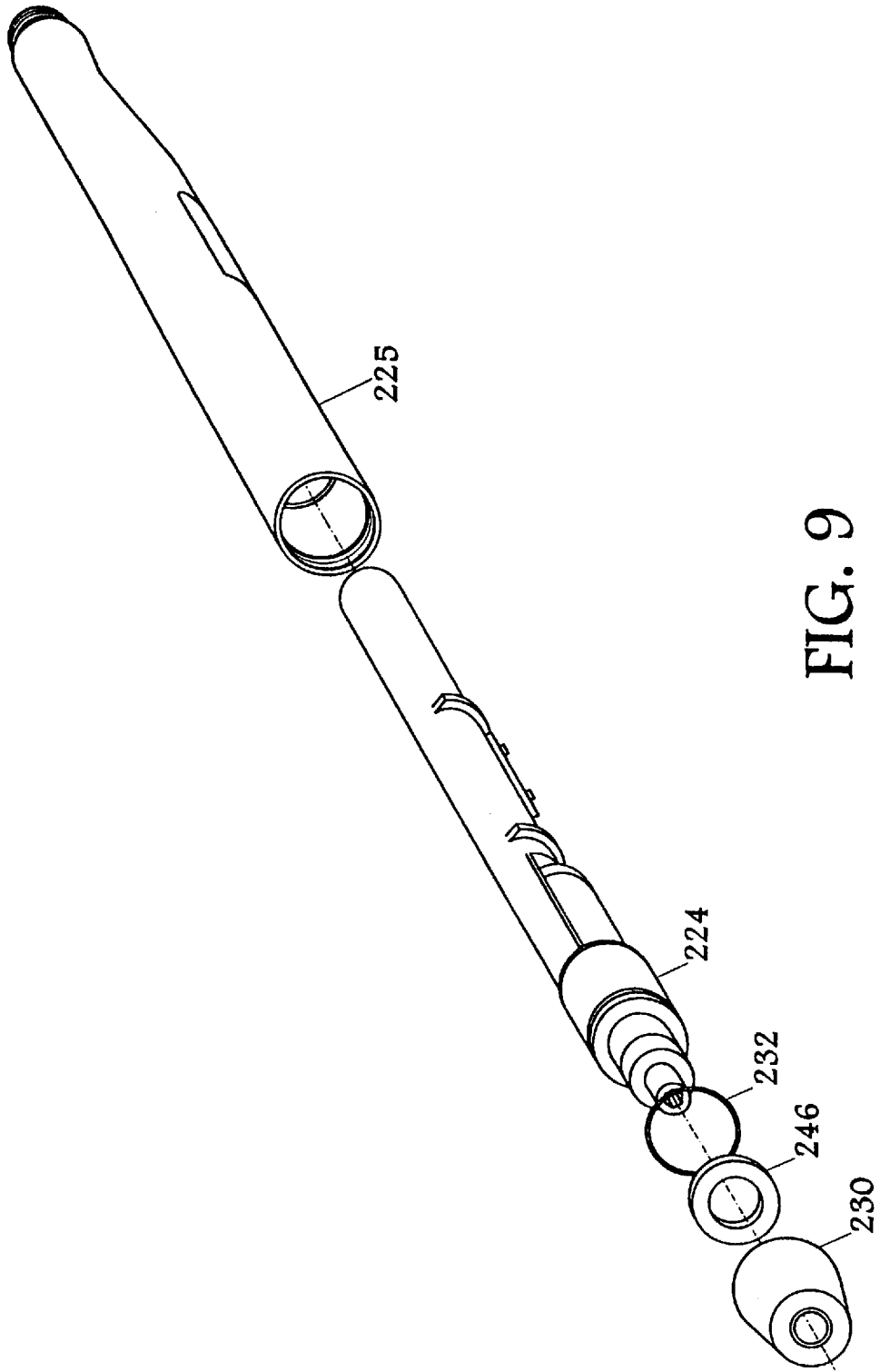
FIG. 9 is an exploded view of the device as shown in FIG. 7.

The power train cartridge is inserted into the shell 225 as shown in FIG. 9, with the output shaft extending from one end of the shell, and through an end cap 230. The power train cartridge is retained within the shell by means of the end cap engaging the shell, such as by threading it onto the shell at one end of the shell. The opposite end of the shell is closed by means of cap 235.

The sealing arrangement for the device is shown in FIG. 7. A seal 242 is provided on the output shaft, along the surface of the output shaft which engages the face of one end of the planetary housing. The shaft seals 242,244 prevent water from entering the power train cartridge between the planetary housing, and the output shaft. A housing seal 246 is provided between the end of the planetary housing and the shell, and an O ring 232 is provided which seal between the planetary housing and the shell. A debris shield 234 aids in preventing water from entering the shell and the power train cartridge, but is primarily present to prevent solid particulate matter from entering the shell and the power train cartridge.

The planetary gear train allows the rotation of the device to be in line with the longitudinal axis of the shell, so that the device can be inserted into restricted spaces, such as glassware, and articulated to scrub foreign materials from glassware and the like. The use of the planetary gear train also allows the motor and battery to be positioned very near the output shaft, so that the weight of the device, and the center of gravity of the device, is within the hand in normal use, so that the device can be articulated in a very desirable manner to aid in removing foreign materials with the brush tool.

Referring now to FIG. 10, various brush tools 50,52,54 may be inserted into the output shaft. The brushes are removably attached to the output shaft, so that brushes of various lengths and configurations may be used.

FIGS. 11 and 12, show a soap dispensing brush 54. The soap dispensing brush is equipped with a valve which is actuated by forcing the brush plate 56 toward an object being cleaned so as to move the plunger 58 to open the spring biased valve 60. Soap or other cleaning material which is present within the brush housing flows through the opening. A removable cap 62 is provided to allow the liquid cleaning material to be replenished as desired.

FIG. 24 shows a bottle brush 70 which may be attached to the output shaft. Brush 70 has a splatter shield 72 which traverses the shaft of the brush to reduce water splatter as the brush rotates. The shield traverses the shaft of the brush as the brush is inserted into an object, such as glassware, thereby retracting the shield out of the way. Spring biasing which affords minimal resistance could be used to return the shield.

Figure 16:
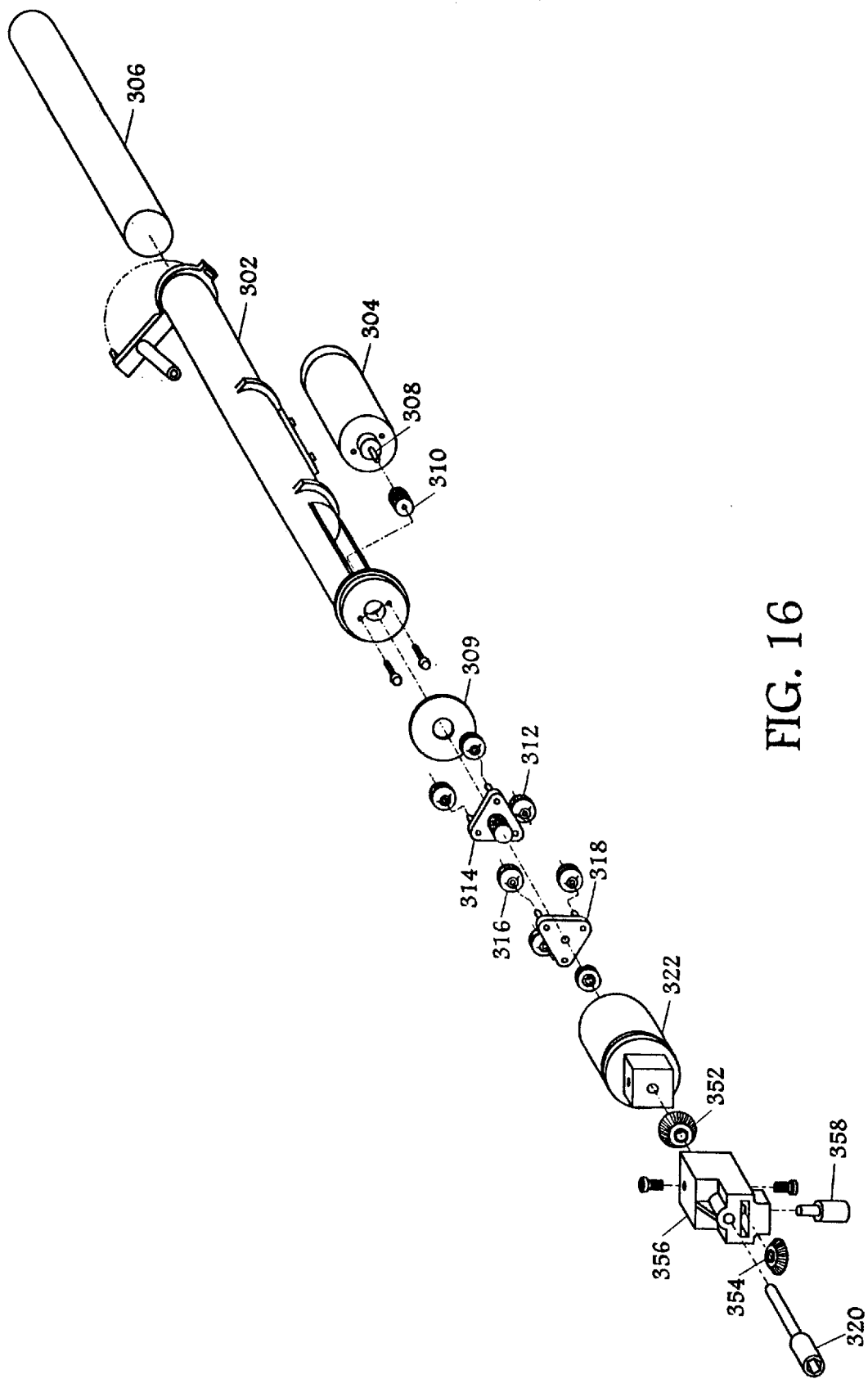
FIG. 16 is an exploded view of the embodiment of the device of FIG. 13.

FIG. 16 shows an exploded view of the power train cartridge of yet another embodiment of the device. A cradle 302 is provided, in which a motor 304 and a rechargeable battery 306 are positioned. The cradle is elongated with the motor positioned near one end thereof, and the battery is positioned in contact with the motor in the opposite end of the cradle. The motor shaft 308 extends through an end plate 309 of the cradle, and a pinion 310 is present on the motor shaft. The pinion engages a set of first stage planetary gears 312. The first stage of planetary gears are positioned on the first stage planetary gear carrier 314. A set of second stage planetary gears 316 is provided, which are positioned on the second stage planetary gear carrier 318. The second stage planetary gear carrier, is, in turn, connected to the primary output shaft 320. The planetary gear train, which is comprised of the first stage planetary gears and the second stage planetary gears, reduces the rotational speed at the output shaft in comparison to the motor, and increases the torque at the output shaft in comparison to the motor.

A planetary gear housing 322 is provided. The planetary gear train is contained within the planetary housing. The planetary housing is connected to the end of the cradle, as shown. The output shaft extends through an end of the planetary housing. The planetary housing, when combined with the cradle, forms a power train cartridge 324. An additional power take off is provided, which is at an angle to the first power take off, so that a brush or tool may be positioned axially, or at an angle to, the rotation of the motor. Gear 352 is fitted to the primary output shaft and rotates with the shaft. Gear 354 is located in gear housing 356, and is driven by gear 352. Secondary output shaft 358 is driven by gear 354, and rotates therewith.

Figure 15:
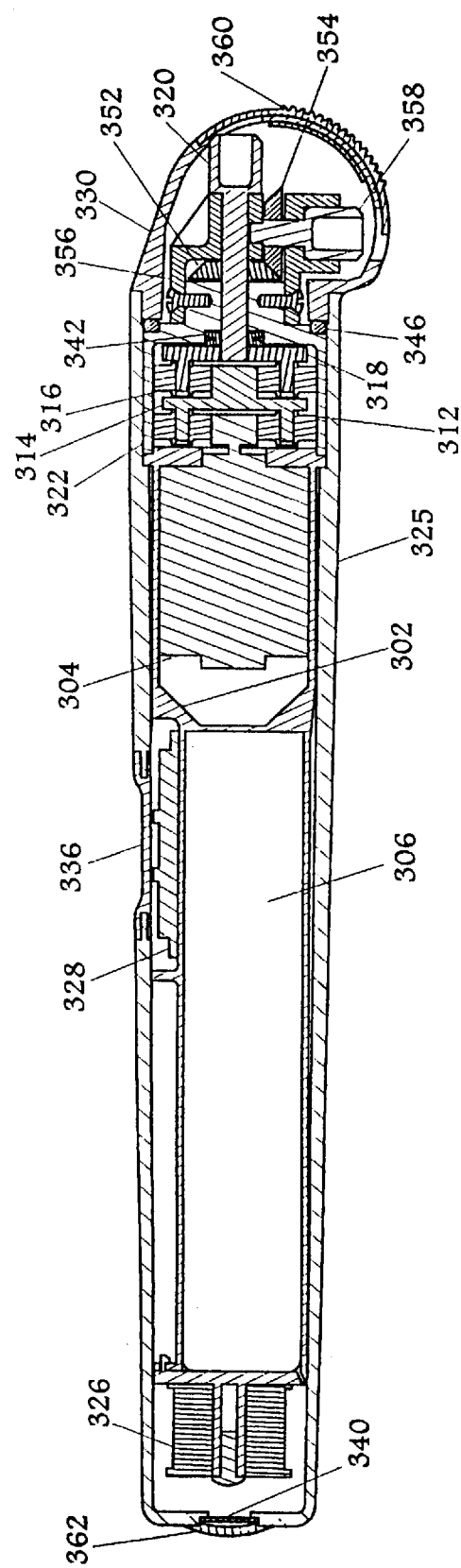
FIG. 15 is a sectioned view of the embodiment of the device shown in FIG. 13.

Referring now to FIG. 15, the power train cartridge has an inductive charging coil 326 mounted to the cradle near the end where the battery is positioned. A switch 328 is provided within the cradle, which may be selectively positioned to allow a current to flow from the battery to the motor, so as to actuate the motor. A switch membrane 336 may be provided as a water seal.

Figure 17:
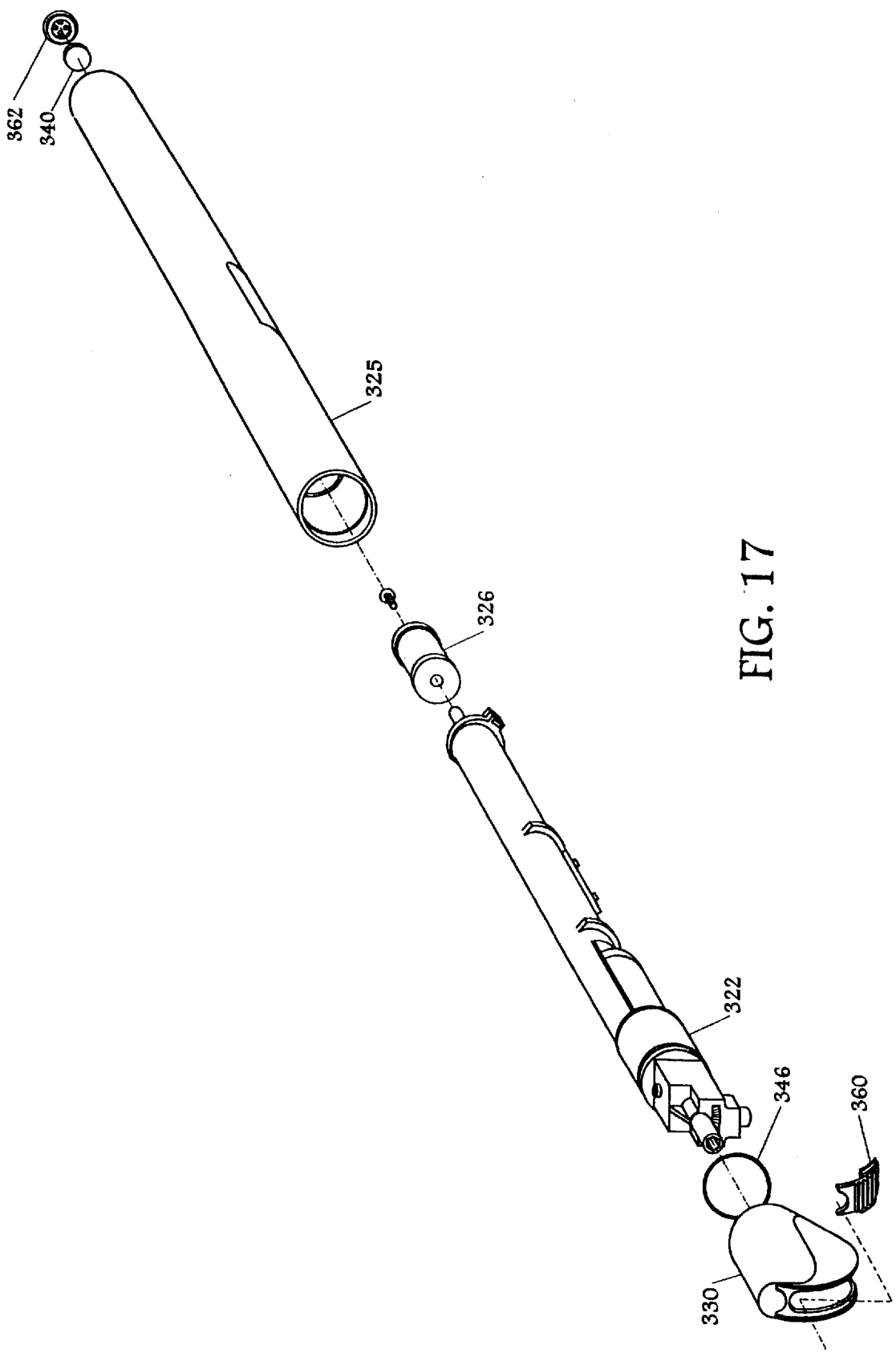
FIG. 17 is an exploded view of the device of the embodiment of FIG. 13.

The power train cartridge is inserted into the shell 325 as shown in FIG. 17, with the output shaft extending into an end cap 330. The power train cartridge is retained within the shell by means of the end cap engaging the shell, such as by threading it onto the shell at one end of the shell. The opposite end of the shell is closed.

A seal 342 is provided on the output shaft, along the surface of the output shaft. The seal prevents water from entering the power train cartridge between the planetary housing, and the output shaft. A housing seal 346 is provided between the end of the planetary housing and the end cap. The seal may be an O ring.

A cover 360 is provided in the end cap. The cover is positioned to allow access to one power output shaft, and to prevent access to the other output shaft. The cover may be slidably mounted to the end cap to selectively allow and deny access to the output shafts.

A valve or gas permeable membrane may be provided within the shell. The valve or gas permeable membrane 340 allows gases to exit the shell, in the event gases accumulate within the shell, for example, as a result of recharging the batteries. The valve or gas permeable membrane prevent water from entering the shell. A protective screen 362 may positioned over the valve or gas permeable membrane.

FIG. 13 shows the device with the cover 360 positioned for access to the primary output shaft 320. FIG. 14 demonstrates the cover 360 positioned for access to the secondary output shaft.

FIGS. 18 and 19 show still another embodiment of the device. This embodiment allows the brush to be articulated relative to the handle of the device for positioning of the brush at various angles.

Figure 22:
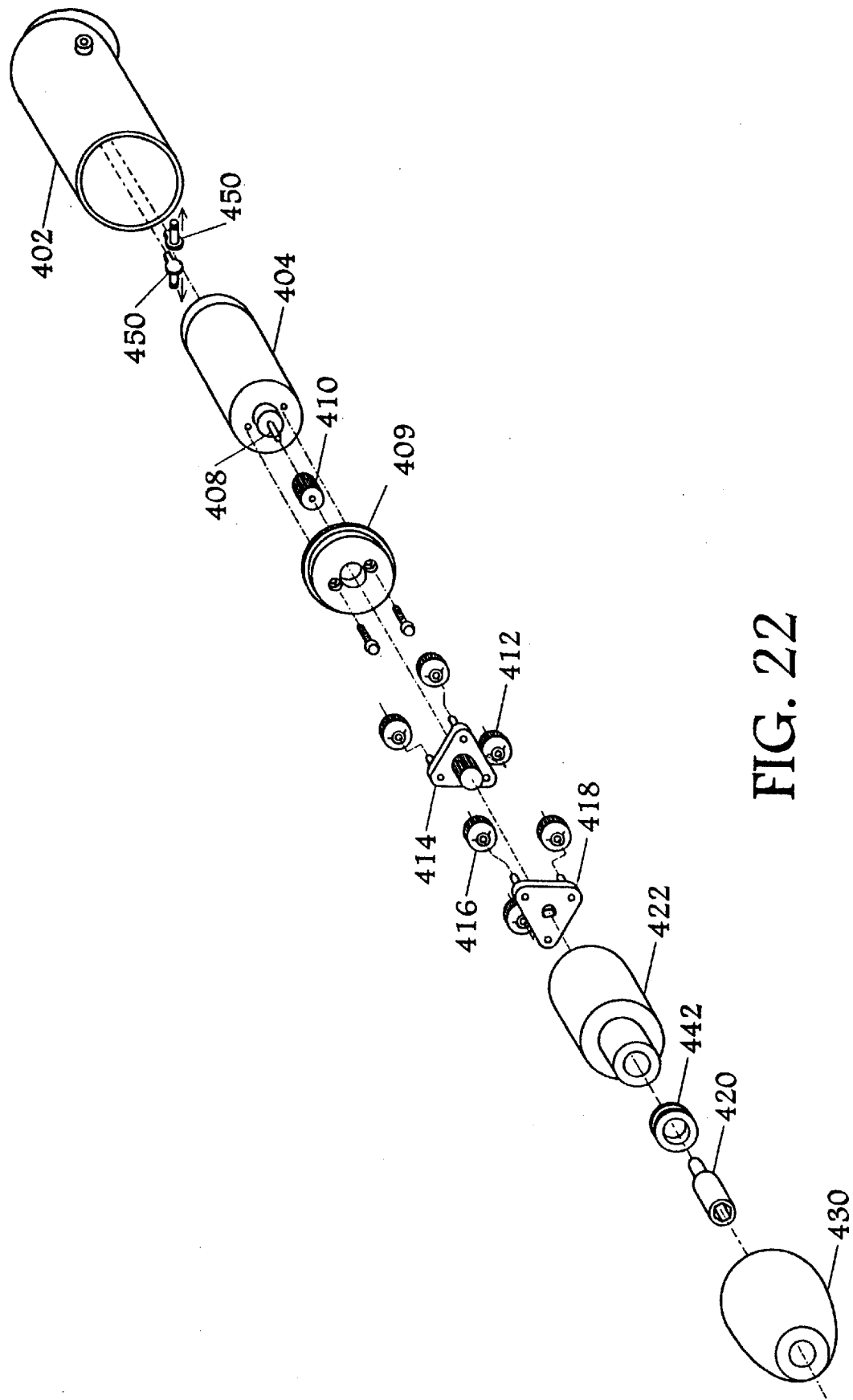
FIG. 22 is an exploded view of the device of the embodiment of FIG. 18.

FIG. 22 shows an exploded view of the power module of the embodiment of FIGS. 18 and 19. A motor housing 402 is provided, in which a motor 404 is positioned. The motor shaft 408 extends through a motor mount 409, and a pinion 410 is present on the motor shaft. The pinion engages a set of first stage planetary gears 412. The first stage of planetary gears are positioned on the first stage planetary gear carrier 414. A set of second stage planetary gears 416 is provided, which are positioned on the second stage planetary gear carrier 418. The second stage planetary gear carrier, is, in turn, connected to the output shaft 420. The planetary gear train, which is comprised of the first stage planetary gear and the second stage planetary gears, reduces the rotational speed at the output shaft in comparison to the motor, and increases the torque at the output shaft in comparison to the motor.

A planetary gear housing 422 is provided. The planetary gear train is contained within the planetary housing. The output shaft extends through an end of the planetary housing.

Figure 21:
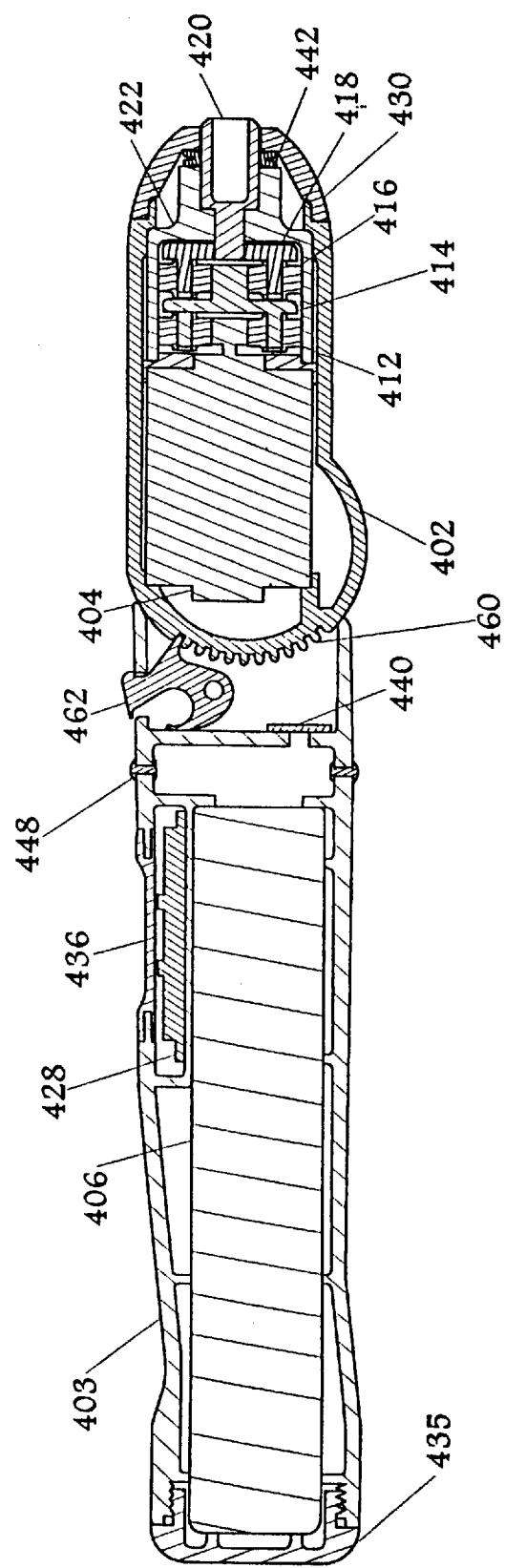
FIG. 21 is an sectioned view taken essentially along line A—A of FIG. 20.

Referring now to FIG. 21, a switch 428 is provided within the shell 403, which may be selectively positioned to allow a current to flow from the battery 406 to the motor, so as to actuate the motor. A switch membrane 436 may be provided as a water seal. Recharging lugs 448 are present on the outside of the shell which are, in turn, connected to the battery.

Figure 20:
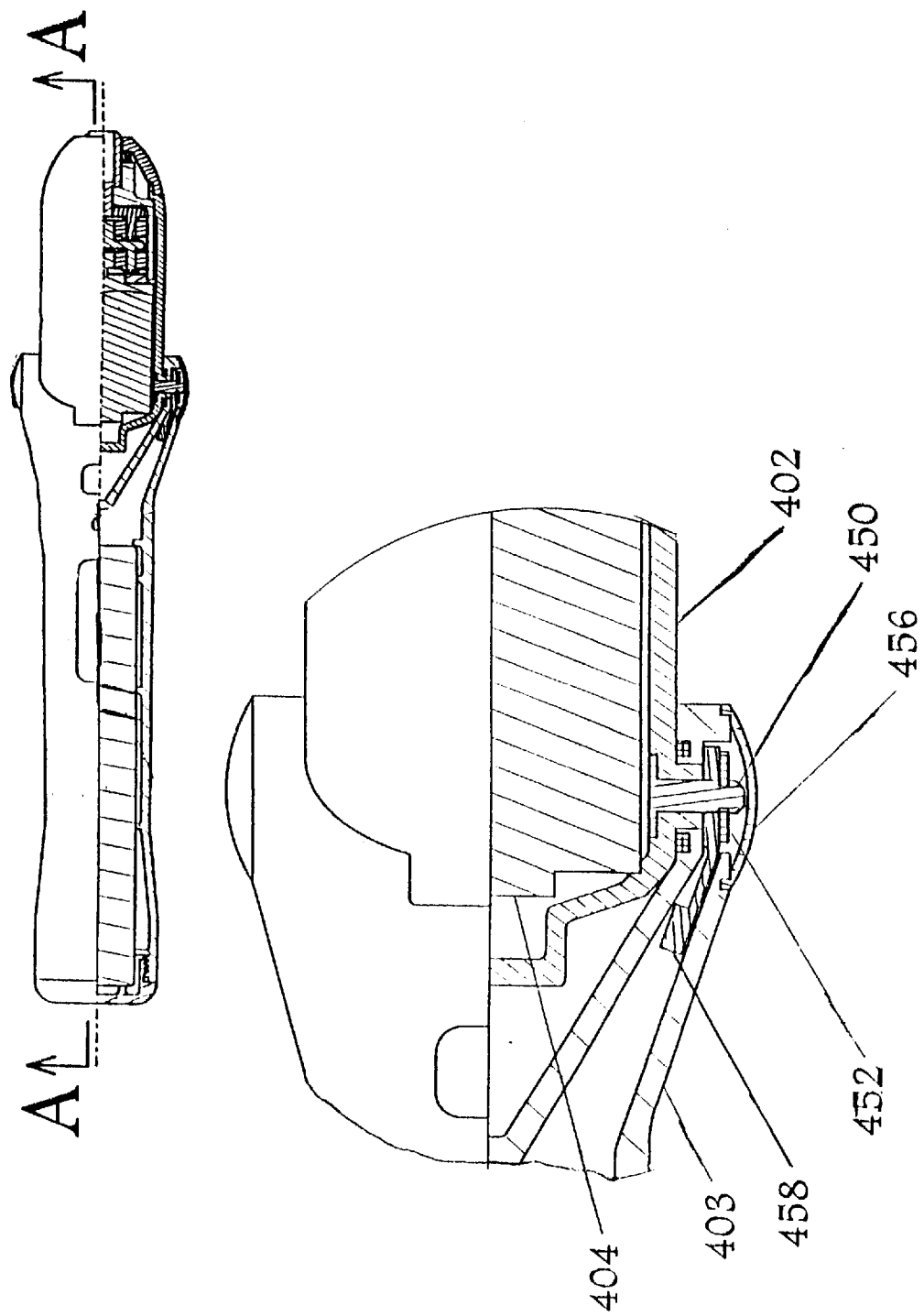
FIG. 20 is a partially sectioned view of the embodiment of the device shown in FIG. 18, with an enlarged isolation.
Figure 23:
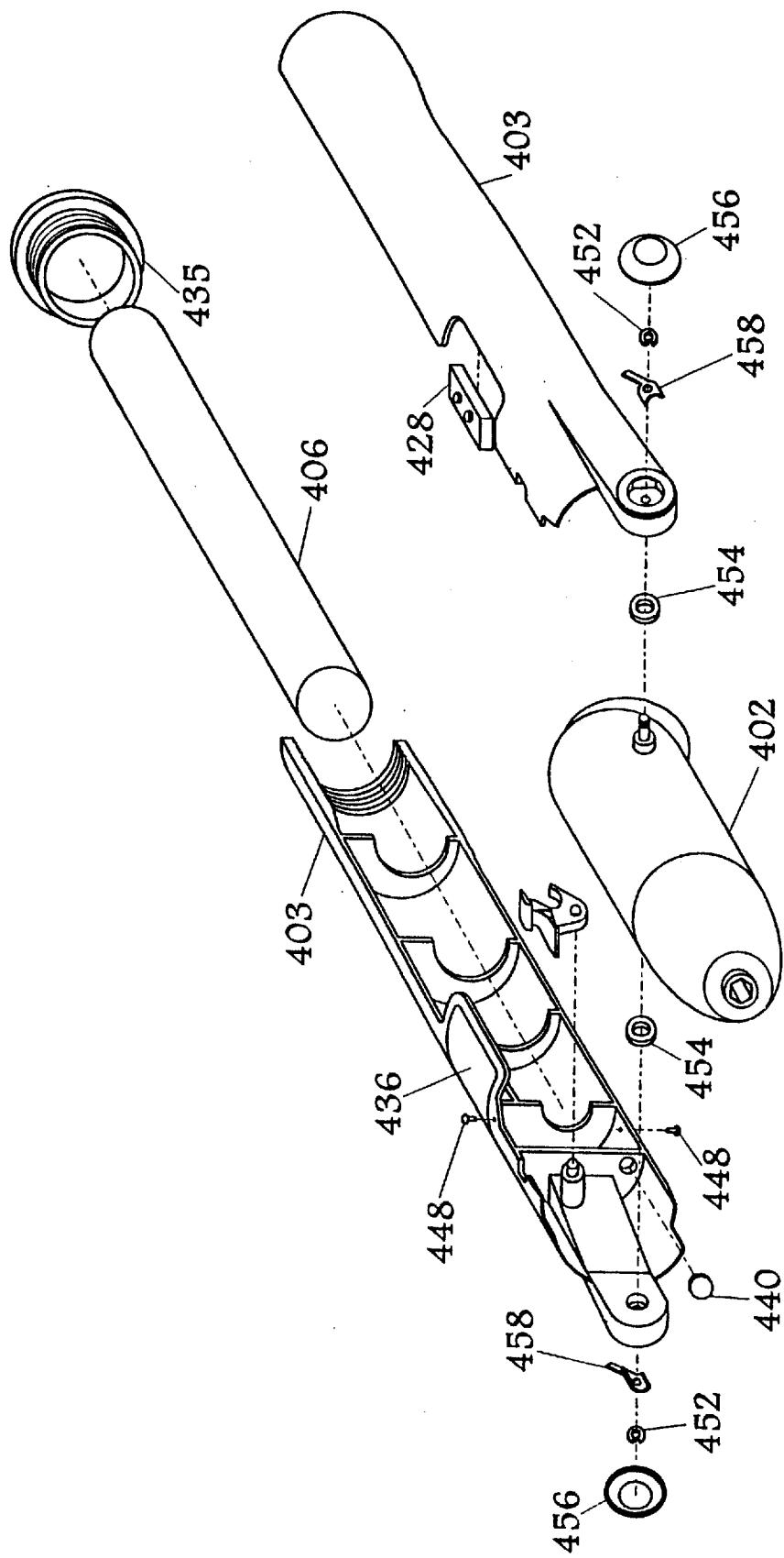
FIG. 23 is an exploded view of the device of the embodiment of FIG. 18.

The power module is connected to the shell as shown in FIGS. 20 and 23, with the output shaft extending through an end cap 430. The opposite end of the shell is closed by means of cap 435.

A seal 442 is provided on the output shaft, along the surface of the output shaft. The seal prevents water from entering the power train cartridge between the planetary housing, and the output shaft.

A valve or gas permeable membrane may be provided within the shell. The valve or gas permeable membrane 440 allows gases to exit the shell, in the event gases accumulate within the shell, for example, as a result of recharging the batteries. The valve or gas permeable membrane prevent water from entering the shell.

The housing 402 is pivotally mounted to the shell 403 to allow the housing to be articulated relative to the shell. Contact pins 450 extending from the housing engage the shell, and the housing pivots relative to the contact pins. The pins 450 are mounted through the housing and shell as demonstrated by FIG. 23 and FIG. 20, and are retained by snap rings 452. Seals 454 are provided between the housing and the shell. Covers 456 are provided over the ends of the pins. The pins extend through spring washer contacts 458, which are used to conduct current from the battery to the motor.

A ratchet is used to control the pivotal relationship between the housing and the shell as shown in FIG. 21. A ratchet 460 is provided on the housing 402 adjacent to the shell. An angle adjustment pawl 462 is pivotally mounted to the shell which engages the ratchet. The pawl may be spring biased. The pawl may be actuated by applying manual pressure to a lever attached to the pawl.

What is claimed is:

1. A battery powered, water submersible, scrubbing device, comprising:
   a. a motor;
   b. a pinion which communicates with, and is driven by, said motor;
   c. at least one reducing gear arrangement which communicates with said pinion and is driven by said motor and said pinion;
   d. an output shaft which communicates with and is driven by said at least one reducing gear arrangement;
   e. a gear housing having an enlarged end in which said at least one reducing gear arrangement is located, having an end through which said output shaft extends;
   f. sealing means which is positioned around said output shaft and which provides a water seal between said output shaft and said gear housing;
   g. a shell in which said gear housing is located;
   h. sealing means which is positioned between said gear housing and said shell; and
   i. scrubbing means which communicates with said output shaft.

2. A battery powered, water submersible, scrubbing device, as described in claim 1, further comprising a second output shaft which communicates with and is driven by said at least one reducing gear arrangement.

3. A battery powered, water submersible, scrubbing device, as described in claim 2, further comprising a cover having means for selectively positioning said cover to allow access to said second output shaft.

4. A battery powered, water submersible, scrubbing device, as described in claim 1, further comprising a cover having means for selectively positioning said cover to allow access to said output shaft.

5. A battery powered, water submersible, scrubbing device, as described in claim 1, wherein a debris shield is mounted to one end of said housing, and wherein said output shaft extends through said debris shield.

6. A battery powered, water submersible, scrubbing device, as described in claim 5, further comprising sealing means which is positioned around said gear housing and which provides a water seal between said shell and said gear housing.

7. A battery powered, water submersible, scrubbing device, as described in claim 6, wherein said scrubbing means is removably mounted to said output shaft.

8. A battery powered, water submersible, scrubbing device, as described in claim 5, wherein said scrubbing means is removably mounted to said output shaft.

9. A battery powered, water submersible, scrubbing device, as described in claim 8, wherein said output shaft has a flange thereon which is located on a portion of said output shaft that extends from said gear housing.

10. A battery powered, water submersible, scrubbing device, as described in claim 5, wherein said output shaft has a flange thereon on a portion of said output shaft that extends from said gear housing.

11. A battery powered, water submersible, scrubbing device, as described in claim 6, wherein said output shaft has a flange thereon on a portion of said output shaft that extends from said gear housing.

12. A battery powered, water submersible, scrubbing device, as described in claim 1, further comprising sealing means which is positioned around said gear housing and which provides a water seal between said shell and said gear housing.

13. A battery powered, water submersible, scrubbing device, as described in claim 12, wherein said scrubbing means is removably mounted to said output shaft.

14. A battery powered, water submersible, scrubbing device, as described in claim 12, wherein said output shaft has a flange thereon on a portion of said output shaft that extends from said gear housing.

15. A battery powered, water submersible, scrubbing device, as described in claim 1, wherein said scrubbing means is removably mounted to said output shaft.

16. A battery powered, water submersible, scrubbing device, as described in claim 15, wherein said output shaft has a flange thereon which is located on a portion of said output shaft that extends from said gear housing.

17. A battery powered, water submersible, scrubbing device, as described in claim 1, wherein said output shaft has a flange thereon on a portion of said output shaft that extends from said gear housing.

18. A battery powered, water submersible, scrubbing device, as described in claim 1, further comprising pressure relief means located in said housing which prevents water from entering said housing and allows trapped gases to exit said housing.

19. A battery powered, water submersible, scrubbing device, comprising:
  a. a housing;
  b. a motor which is located in said housing;
  c. an output shaft which communicates with, and is driven by, said motor;
  d. sealing means which is positioned around said output shaft and which provides a water seal between said output shaft and said housing;
  e. a shell having at least one battery located therein, wherein said shell is pivotally connected to said housing; and
  f. scrubbing means which communicates with said output shaft.

20. A battery powered, water submersible, scrubbing device, as described in claim 19, further comprising means for causing said housing to pivot relative to the shell.

21. A battery powered, water submersible, scrubbing device, as described in claim 20, further comprising pressure relief means located in said housing which prevents water from entering said housing and allows trapped gases to exit said housing.

22. A battery powered, water submersible, scrubbing device, as described in claim 19, further comprising pressure relief means located in said housing which prevents water from entering said housing and allows trapped gases to exit said housing.

* * * * *